United States Patent [19]

Beck et al.

[11] Patent Number: 5,194,255

[45] Date of Patent: * Mar. 16, 1993

[54] ANTIHYPERTENSIVE HYPERIMMUNE MILK, PRODUCTION, COMPOSITION, AND USE

[75] Inventors: Lee R. Beck; Ralph J. Stolle, both of Lebanon, Ohio

[73] Assignee: Stolle Research & Development Corporation, Cincinnati, Ohio

[*] Notice: The portion of the term of this patent subsequent to Nov. 7, 2006 has been disclaimed.

[21] Appl. No.: 431,773

[22] Filed: Nov. 6, 1989

Related U.S. Application Data

[60] Continuation of Ser. No. 161,039, Feb. 26, 1988, Pat. No. 4,879,110, which is a continuation-in-part of Ser. No. 1,848, Jan. 9, 1987, Pat. No. 4,897,265, which is a division of Ser. No. 546,162, Oct. 27, 1983, Pat. No. 4,636,384, which is a continuation-in-part of Ser. No. 384,625, Jun. 3, 1982, abandoned.

[51] Int. Cl.⁵ ............................................. A61K 35/20
[52] U.S. Cl. ...................................... 424/87; 424/535
[58] Field of Search ................................ 424/87, 535

[56] References Cited

U.S. PATENT DOCUMENTS

| | | | |
|---|---|---|---|
| 3,128,230 | 4/1964 | Heinbach | 424/85 |
| 3,376,198 | 4/1968 | Petersen et al. | 424/85 |
| 3,911,108 | 10/1975 | Singh | 424/86 |
| 4,284,623 | 8/1981 | Beck | 424/85 |
| 4,324,782 | 4/1982 | Beck | 424/87 |
| 4,636,384 | 1/1987 | Stolle et al. | 424/87 |
| 4,732,757 | 3/1988 | Stolle etal. | 424/87 |
| 4,879,110 | 11/1989 | Beck et al. | 424/85.8 |
| 4,897,265 | 1/1990 | Stolle et al. | 424/87 |
| 4,956,349 | 9/1990 | Beck | 424/535 |

FOREIGN PATENT DOCUMENTS

| | | |
|---|---|---|
| 587849 | 12/1959 | Canada . |
| 0300102 | 1/1989 | European Pat. Off. . |
| 1211876 | 11/1970 | United Kingdom . |
| 1442283 | 7/1976 | United Kingdom . |
| 1505513 | 3/1978 | United Kingdom . |

OTHER PUBLICATIONS

Rudd, P. et al. in Gilman, A. G. et al., eds., *The Pharmacological Basis of Therapeutics*, McMillan, New York (1980) pp. 784-805.

*Primary Examiner*—Merrell C. Cashion, Jr.
*Assistant Examiner*—Choon P. Koh
*Attorney, Agent, or Firm*—Sterne, Kessler, Goldstein & Fox

[57] ABSTRACT

The invention relates to a method for inducing the production of a milk anti-hypertensive factor in an animal, to a method for the isolation of said factor from the milk of said animal in a substantially pure form, and to the use of said factor to treat hypertension in humans and other animals, and to compositions containing the antihypertensive factor.

2 Claims, 4 Drawing Sheets

ANTIHYPERTENSIVE HYPERIMMUNE MILK, PRODUCTION, COMPOSITION, AND USE

CROSS-REFERENCES TO RELATED DOCUMENTS

The present application is a continuation of Ser. No. 161,039, filed Feb. 26, 1988, now U.S. Pat. No. 4,879,110, which is a continuation-in-part of application Ser. No. 001,848, filed Jan. 9, 1987, now U.S. Pat. No. 4,897,265, which is a division of application Ser. No. 546,162, filed Oct. 27, 1983, now U.S. Pat. No. 4,636,384, which is a continuation-in-part of application Ser. No. 384,625, filed Jun. 3, 1982, now abandoned.

BACKGROUND OF THE INVENTION

1. Field of the Invention

This invention relates to the production of a biologic composition that reduces blood pressure, and to the use of such compositions in lowering elevated arterial pressure in subjects.

2. Description of the Background Art

An elevated arterial pressure (i.e., hypertension, high blood pressure) is probably the most important public health problem in developed countries—being common, asymptomatic, readily detectable, and often leading to lethal complications if left untreated. Williams, G. H., et al.. In: Harrison's Principles of Internal Medicine, 10th ed., Petersdorf, R. G., et al.. eds., McGraw-Hill, New York, 1983, chapter 247.

Hypertensive patients are classified into two broad categories. A relatively small proportion of patients develop hypertension as a manifestation of an identifiable and specifically treatable underlying cause, such as pheochromocytoma, renal arterial stenosis, or endocrine disease. Such patients are denominated as exhibiting secondary hypertension.

From 80–95% of patients with sustained elevated arterial pressure have no discernible underlying causative factor. These patients are said to have essential or primary or idiopathic hypertension.

The etiology of essential hypertension is almost certainly multifactorial. Such factors include the sympathetic and parasympathetic nervous systems, baroreceptor function, and the reninangiotensin-aldosterone and the atrial natriuretic factor systems that control renal sodium and water flux. In addition, genetic and cardiovascular risk factors such as obesity, hypercholesterolemia, diabetes, salt intake, occupation, and cigarette smoking have long been assumed to be important in the genesis of essential hypertension.

Whatever the etiology of the disease, patients with untreated hypertension die prematurely, most commonly due to heart disease, but with strokes and renal failure often frequently occurring. As a result of clinical trials, there is firm evidence that reducing diastolic blood pressure that is above 90 mm Hg in middle-aged patients is associated with a decrease in cardiovascular morbidity and mortality. Blaschke, T. F., et al.. In: Goodman and Gilman's The Pharmacological Basis of Therapeutics, Gilman, A. G., et al.. eds., McMillan, New York, 1980, chapter 32.

Current treatments of hypertension consist of general measures and specific measures. General measures include dietary control and elimination of cardiovascular risk factors such as overweight, cigarette smoking, high salt intake, stress, etc.

Specific measures for treating hypertension consist of therapy with antihypertensive drugs. Many clinical studies have demonstrated that in almost all cases of hypertensive cardiovascular disease, the blood pressure can be successfully controlled by skillful use of the drugs currently available. However, it has also been estimated that only a small percentage of all hypertensive patients under treatment are even close to optimal control. Thus, effective use of antihypertensive drugs is not "routine," and therapy must be tailored to the individual patient and be adjusted as necessary to maintain an optimal balance between the therapeutic effects and the well-known adverse side effects associated with currently-employed antihypertensive drugs. Blaschke et al.. supra at 809.

There are four classes of hypertensive drugs currently being used, each directed to a different mechanism of disease. These classes include: diuretics, anti-adrenergic agents, vasodilators, and angiotensin blockers. Each is therapeutically effective in appropriate patients, but each may produce severe adverse side effects; all are expensive.

The popular thiazine diuretics are quickly effective, but may produce undesirable side effects such as hypokalemia, hypouricemia, and carbohydrate intolerance. Anti-adrenergic drugs (i.e., "beta blockers") are effective in certain types of hypertension, i.e., when there is increased cardiac sympathetic nerve activity, but such drugs may precipitate congestive heart failure and asthma, and must be used with caution in diabetics; other side effects include dizziness, depression, nausea, vomiting, diarrhea, and constipation. Vasodilators, which act primarily on arterial resistance rather than on venous capacitance, are effective against hypertension, but the effects of such agents are unfortunately negated by reflex increases in sympathetic discharges that raise heart rate and cardiac output. Thus, vasodilators are contraindicated in severe coronary artery disease, and are also known to produce undesirable side effects such as headache, tachycardia, angina pectoris, anoxia, nausea, vomiting, diarrhea, and a lupus-like syndrome. Angiotensin blockers are promising, but frequent side effects include leukopenia, pancytopenia, proteinuria, nephrotic syndrome, rash, fever, and loss of taste. Williams et al.. supra at 1485.

In all but the mildly hypertensive patient who responds favorably to a diuretic or to a beta blocker, combinations of drugs are used. A successful combination is one whose components give additive or synergistic therapeutic effects, while causing minimal toxicity. Ideally, therapy should lower blood pressure effectively without producing side effects that become so unacceptable to the patient that compliance to the regimen is threatened or that compromise of the vital functions of the brain, heart, or kidneys.

A very difficult and important problem in the drug therapy of hypertension is to determine what constitutes "acceptable" side effects. All the effective antihypertensive drugs can produce quite significant adverse effects, to the extent where, in clinical trials, patients reported feeling better with the placebo than with the antihypertensive drug. Blaschke et al.. supra at 809.

In view of these shortcomings, the limitations to the antihypertensive drug therapy known to the prior art are readily apparent. It would be highly desirable, therefore, to have an antihypertensive agent that is inexpensive, readily available, derived from a natural source, easily administered, highly effective against hypertension, and devoid of undesirable side effects. The hyperimmune bovid milk of the present invention is such an antihypertensive agent.

It has been known in the prior art to produce milk having a variety of therapeutic effects. Beck, for example, has disclosed a milk containing antibody to *Staphylococcus mutans* that has dental caries-inhibiting effects (Beck, U.S. Pat. No. 4,324,784; British Patent 1,505,513). The milk is obtained by hyperimmunization of a cow with *Streptococcus mutans* antigen and collecting the therapeutic milk therefrom. Beck has also described a milk having anti-arthritic properties (copending U.S. application Ser. No. 875,140, filed Feb. 6, 1978), and has patented a method of treating inflammation using milk from hyperimmunized cows (Beck, U.S. Pat. No. 4,284,623). Stolle has disclosed a method of using milk from a hyperimmunized cow to treat diseases of the vascular and pulmonary systems (Stolle et al.. U.S. Pat. No. 4,636,384). Heinbach, U.S. Pat. No. 3,128,230, has disclosed milk containing alpha, beta and gamma globulins against anti-9-enic haptens. Singh (U.S. Pat. No. 3,911,108), Peterson (U.S. Pat. No. 3,376,198 and Canadian Patent 587,849), Holm (U.S. Application (published) Ser. No. 628,987), Tannah et al. (British Patent 1,211,876), and Biokema S. A. (British Patent 1,442,283) have also described antibody-containing milks. Steffkoff et al., *Minerva Medica* Italy) 56:4163–4 (1965) have described the treatment of hypertensive diseases with sour milk.

It is well known to those skilled in the art of immunology that serum globulin fractions consisting of various antibody types such as IgA, IgG, and IgM can be used to counter the corresponding antigens, thereby neutralizing the effects of the antigens. There is an almost infinite number of harmful antigens to which animals can be exposed, including carcinogenic, bacterial, viral, and regulatory factors of plant and animal origin, as well as toxins and poisons.

Normally, upon exposure to a foreign antigen, e.g., a bacterium, the immune system of the host will produce antibodies that will neutralize the effects of the antigen. Exposure to such foreign antigens can occur either naturally, or deliberately by administration of the antigen in vaccine form. The latter is generally referred to as active immunization of the host species exposed to the antigen. The antibodies produced in response to such vaccination are homologous to said given species of animal, and are epitopic to the antigen.

In copending related patent applications, U.S. application Ser. No. 546,162, filed Oct. 27, 1983, and U.S. application Ser. No. 001,848, filed Jan. 9, 1987, there was disclosed a method of lowering blood lipid levels and treating lipid-associated vascular disorders, as well as treating macrophage-related pulmonary disorders, comprising feeding test animals and humans antibody-containing milk derived from cows maintained in a hyperimmune state by injections of polyvalent antigens derived from mixtures of killed bacteria. In another copending application (U.S. application Ser. No. No. 069,139, filed Jul. 2, 1987), there was disclosed use of antibody-containing milk derived from hyperimmunized cows for the treatment of gastrointestinal disorders. The present invention is a further development over the inventions disclosed and claimed in the aforementioned applications, the entire disclosures of which are herein incorporated by reference.

All of these references, however, relate only to the isolation from hyperimmunized animals of immunoglobulins raised against various antigens and to the subsequent use of said antigens for either diagnostic procedures, homologous or heterologous passive immunization, or active immunization. No suggestion or speculation is made in any of these references that milk derived from hyperimmunized bovids is useful in lowering arterial blood pressure.

SUMMARY OF THE INVENTION

The present inventors have previously disclosed hyperimmune bovid milk with anti-inflammatory effects and with beneficial effects against vascular, pulmonary, and gastrointestinal disorders.

The beneficial vascular effects of the hyperimmune bovid milk prompted the present inventors to investigate possible effects of the milk on elevated arterial pressure in humans and other animals.

With this in mind, the inventors then made the unexpected discovery that milk obtained from cows hyperimmunized against certain bacterial antigens (i.e., the hyperimmune milk of the invention), when administered orally to hypertensive subjects, dramatically decreased the blood pressure to normotensive values, and did so without any detectable undesirable side effects. It was also discovered that milk of non-hyperimmunized cows also contains anti-hypertension activity, but that this activity is greatly enhanced by the hyperimmunization of the donor cow.

Therefore, the invention relates to a method of production of hyperimmune bovid milk, a composition of said milk suitable for administration to a subject, and to the use of said composition to reduce elevated arterial pressure in such subjects.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
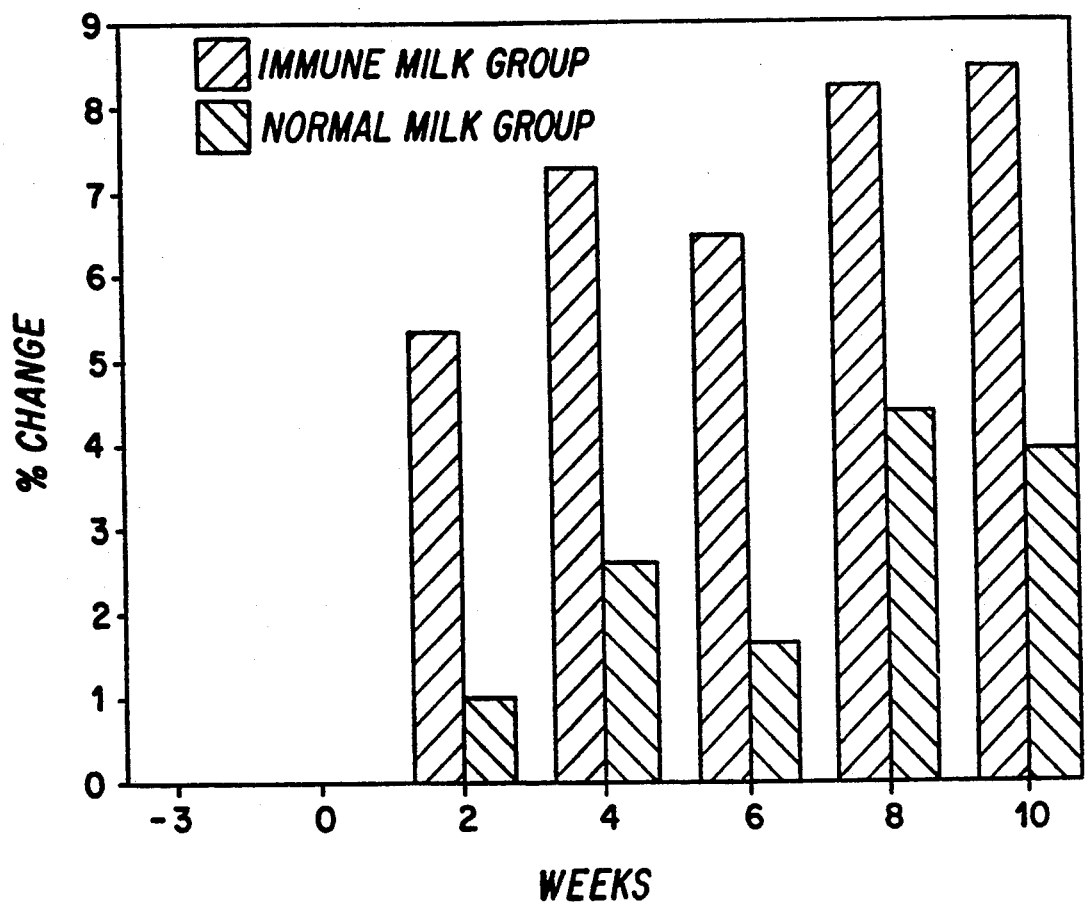
FIG. 1 shows the mean percent change in systolic blood pressure in human subjects drinking control milk and hyperimmune milk.

The invention comprises a natural food product (milk) that has anti-hypertensive properties, a method for producing the same, and a method of use in treating subjects with elevated arterial pressure. The invention represents a significant advance in the state of the art of anti-hypertensive pharmacology because the product of this invention has no adverse side effects. Anti-hypertensive milk can be used to treat hypertension associated with any disease in animals and humans without fear of side effects because it is a natural food product. Examples of human disease conditions which may be treated with anti-hypertensive milk include: primary or secondary hypertension of whatever etiology. By the term "hypertension" is intended, for the purpose of this invention, elevated diastolic arterial pressure of at least 90 mm Hg. By the term "anti-hypertensive factor" is intended a factor obtained in hyperimmune milk with arterial pressure lowering activity. Hyperimmunization of the milk-producing animal provides for a supranormal concentration of anti-hypertensive factor in the milk sufficient to enable its use therapeutically. By the term "hyperimmune milk" is intended, for the purpose of this invention, milk obtained from milk-producing animals maintained in a hyperimmune state, the details for hyperimmunization being described in greater detail below. By the term "supranormal concentration of anti-hypertensive factor" is intended a concentration greater than existing in the milk of a non-hyperimmunized animal.

By the term "milk-producing animal" is intended, for the purpose of this invention, mammals that produce milk in commercially feasible quantities, preferably cows, sheep, and goats, more preferably dairy cows of the genus Bos (bovid), particularly those breeds giving the highest yields of milk, such as Holstein.

By the term "bacterial antigen" is intended, for the purpose of this invention, a lyophilized preparation of heat-killed bacterial cells.

By the term "treating" is intended, for the purpose of this invention, that the symptoms of the disorder be ameliorated or completely eliminated. By the term "administered" is intended, for the purpose of this invention, any method of treating a subject with a substance, such as orally, intranasally, parenterally (intravenously, intramuscularly, or subcutaneously), or rectally, in a pharmaceutically acceptable vehicle. By the term "animal" is intended, for the purpose of the invention, any living creature that is subject to hypertension, including humans and animals.

The invention is based on the discovery that when a bovid is brought to a specific state of immunization by means of periodic booster administrations of an antigen or mixture of antigens, the bovid will produce milk which has highly beneficial properties in the treatment of hypertension. The beneficial milk properties are enhanced when the bovids are immunized. The induction of immune sensitivity alone is insufficient to enhance the antihypertensive properties in milk, as is shown by the fact that normal cows' milk contains a lower level of activity than milk from hyperimmunized cows, even though cows have become sensitized against various antigens during normal immunization against cow diseases.

The anti-hypertensive properties of milk are maximized in milk produced by bovids maintained in the immune state by booster injections. Hyperimmunization is achieved by administering periodic boosters with sufficiently high doses of antigens or mixtures of antigens. The preferred dose range should be equal to or greater than 50% of the dosage necessary to cause primary sensitization of the bovid. Thus, there is a booster dosage threshold below which the maximum properties are not produced in the cow, even though the cow may be in what is normally called an immune state. In order to achieve the hyperimmune state, it is essential to test the bovid's milk after a first series of booster administrations. If the milk does not contain the desired properties, a second series of boosters of higher dosage has to be administered. This process is repeated until the maximum properties appear in the milk. The process of producing the hyperimmune milk has been disclosed in U.S. Pat. No. 4,284,623 to Beck, which is herein incorporated by reference to the extent that it provides details of the production of hyperimmune milk. In summary, the process comprises the following steps:

1. Antigen selection.
2. Sensitization of the bovid by primary immunization.
3. Testing the serum of the bovid to confirm sensitivity induction.
4. Administering boosters of appropriate dosage to induce and maintain a hyperimmune state.
5. Testing anti-hypertensive properties of the milk.
6. Collecting milk from the bovid during the hyperimmune state.

The milk of the invention can be collected by conventional methods; however, special processing is necessary to protect the biological properties of the milk. Low temperature pasteurization is required; the pasteurization temperature should not exceed 140° C. Following pasteurization, the fat is removed by standard procedures. The milk is concentrated and spray-dried. The skim milk is concentrated under vacuum at low temperatures so as not to destroy the anti-hypertensive factor. (See e.g. Kozakowski, F., "Cheese and Fermented Milk Products", 2d Edition, 1977). The final product is a milk powder which has anti-hypertensive properties.

Fluid milk can also be used, of course, as well as concentrated milk products or a fraction of the milk containing the biologically-active factor, such as the acid whey fraction. By the term "whey" is intended, for the purpose of this invention, milk from which cream and caseinaceous material has been separated.

The milk of the invention can be provided in any amount which affects the decrease of hypertensive conditions in animals. Daily amounts, equivalent to 1 ml to 10 liters of whole fluid milk, can be provided, depending on the particular circumstances of the hypertension and the animal species. The preferred dose is 0.5–1.0 g of skim milk powder per kg of body weight.

The fat-free milk can, of course, be incorporated into any food product as long as the food product is not treated at a temperature which is too elevated and would inactivate the anti-hypertensive properties of the product. A temperature lower than 140° C. is preferred. For example, puddings or yogurt may be prepared with anti-hypertensive milk.

Further, when the fat-free milk is treated with rennet, and the casein is separated after precipitation thereof, it is found that the sweet-whey supernatant fraction contains the anti-hypertensive factor. This sweet-whey factor may also be added to syrups, ice cream mixes, candy, beverages, cattle feeds or the like. (See, Kozakowski, supra, at 446).

The process of producing the hyperimmune milk containing supranormal levels of anti-hypertensive factor is as follows. In summary, one process of producing the hyperimmune milk containing supranormal levels of anti-hypertensive factor comprises the following steps: (1) antigen selection; (2) primary immunization of the bovid; (3) testing the serum to confirm sensitivity induction; (4) hyperimmunization with boosters of appropriate dosage; and optionally, (5) testing the milk for anti-hypertensive properties; (6) collecting the milk from the hyperimmune bovid; and (7) processing the milk to fractionate the anti-hypertensive factor.

Step 1: Any antigen or combination of antigens may be employed. The antigens can be bacterial, viral, protozoan, fungal, cellular or any other substances to which the immune system of a milk-producing animal will respond. The critical point in this step is that the antigen(s) must be capable, not only of inducing immune and hyperimmune states of the milk producing animal, but also of producing supranormal levels of anti-hypertensive factor in the milk. Preferably, polyvalent bacterial agents are used. One preferred vaccine is a mixture of polyvalent bacterial antigens, described in detail in Example 1 below.

Step 2: The antigen(s) can be administered in any method that causes sensitization. In one method, a vaccine composed of antigen derived from $1 \times 10^6$ to $1 \times 10^{20}$, preferably $10^8$ to $10^{10}$, most preferably $2 \times 10^8$, heat-killed bacteria is administered by intramuscular injection. However, other methods such as intravenous injection, intraperitoneal injection, rectal suppositories, or oral administration may be used.

Step 3: It is necessary to determine whether or not the milk-producinganimal has become sensitive to the antigen. There are a number of methods known to those skilled in the art of immunology to test for sensitivity (*Methods in Immunology and Immunochemistry*, Williams, C. A. et al.. Academic Press, New York, Volumes 1-5 (1975)). The preferred method is to use a polyvalent vaccine comprising multiple bacterial species as the antigen and to test for the presence of agglutinating antibodies in the serum of the animal before and after challenge with the vaccine. The appearance of milk antibodies after immunization with the vaccine indicates sensitivity; at this point, it is possible to proceed to step 4.

Step 4: This involves the induction and maintenance of the hyperimmune state in the sensitized animal. This is accomplished by repeated booster administration at fixed time intervals of the same polyvalent vaccine that was used to achieve the primary sensitization. A two-week booster interval is optimal for polyvalent bacterial antigens. However, it is necessary to insure that the animal does not pass from a hyperimmune state to a state of immune tolerance to the antigen.

In a preferred embodiment, hyperimmunization of bovids may be achieved by a single administration of microencapsulated vaccine, prepared as described in detail in Example 1B below.

In an alternative embodiment, it is possible to combine different immunization procedures, e.g., simultaneously administering microencapsulated and liquid antigen, or intramuscular injection for primary immunization, and booster doses by oral administration or parenteral administration by microencapsulation means. Many different combinations of primary and hyperimmunization are known to those skilled in the art.

Step 5: It is necessary to test the milk for anti-hypertensive activity levels. This can be accomplished by any research technique that tests the effects of either the hyperimmune milk or products derived therefrom upon hypertension.

Step 6: This involves the collection and processing of the milk. The milk can be collected by conventional methods. Fractionating the milk to obtain the anti-hypertensive factor can then be carried out.

Step 7: The general method of isolation and purification of the anti-hypertensive factor from hyperimmune milk is as follows: (1) the milk is defatted to produce skim milk; (b) optionally, casein is removed from the skim milk to produce whey; (c) macromolecules of molecular weight $>10,000$ daltons are removed from the whey; (d) the product from the previous step is fractionated on an ion-exchange column to obtain negatively-charged molecules having molecular weights 10,000 daltons; (e) the milk anti-hypertensive factor-containing, $<100,000$ dalton fraction can be size fractionated on a molecular sieve gel; (f) increasing the pH of the $<10,000$ dalton fraction to alkaline values of about 9 to 12, preferably 10.5, and collecting the precipitate which contains the Milk Anti-Hypertensive Factor (abbrev. MAF); and (g) lyophilizing the precipitate from the previous step.

The invention is based in part upon the unexpected discovery that an anti-hypertensive factor, found normally in milk but produced in large quantities by hyperimmunizing a milk-producing animal against a bacterial antigen vaccine, is effective in treating a variety of hypertensive processes in humans and animals, including dogs. The vaccine used to hyperimmunize the animals does not contain anti-hypertensive activity. It is surprising therefore, that treatment with a milk factor, obtained from animals immunized against a mixed killed bacterial antigen vaccine, is effective in elevating or eliminating hypertensive processes.

Having now described the invention in general terms, the same will be further described by reference to certain specific examples that are provided herein for purposes of explanation only, and are not intended to be limiting unless otherwise specified.

Preparation of Milks

EXAMPLE 1A

Preparation of Mixed Bacterial Vaccine

A bacterial culture, containing the spectrum of bacteria shown in Table 1 below as obtained from the American Type Culture Collection, was reconstituted with 15 ml of growth medium and incubated overnight at 37° C. Once good growth was obtained, approximately one-half of the bacterial suspension was employed to inoculate one liter of broth, with the inoculate being incubated at 37° C. The remaining suspension was transferred to sterile glycol tubes and stored at $-20°$ C. for up to six months.

After good growth was visible in the culture, bacterial cells were harvested by centrifugation of the suspension for 20 minutes to remove the growth medium. The bacterial pellet obtained was resuspended in sterile saline solution and the bacterial sample was centrifuged three times to wash the medium from the cells. After the third sterile saline wash, the bacterial pellet obtained upon centrifugation was resuspended in a small amount of double distilled water.

The medium-free bacterial suspension was heat-killed by placing the suspension in a glass flask in an 80° C. water bath overnight. The viability of the broth culture was tested with a small amount of heat-killed bacteria, as follows: broth was inoculated with heat-killed bacteria, incubated at 37° C. for five days and checked daily for growth. For the safety of the cow, the bacteria should be killed for use in the vaccine.

The heat-killed bacteria were lyophilized until dry. The dry bacteria were then mixed with sterile saline solution to a concentration of about $2.2 \times 10^8$ bacterial cells/ml saline (1.0 optical density units at 660 nm).

TABLE I

Bacteria List

| Name | Media | Gram + or − | ATTC # |
|---|---|---|---|
| 1. Staph. aureus | BHI | + | 11631 |
| 2. Staph. epidermidis | BHI | + | 155 |
| 3. Strep. pyogenes, A. Type 1 | APT | + | 8671 |
| 4. Strep. pyogenes, A. Type 3 | APT | + | 10389 |
| 5. Strep. pyogenes, A. Type 5 | APT | + | 12347 |
| 6. Strep. pyogenes, A. Type 8 | APT | + | 12349 |
| 7. Strep. pyogenes, A. Type 12 | APT | + | 11434 |
| 8. Strep. pyogenes, A. Type 14 | APT | + | 12972 |
| 9. Strep. pyogenes, A. Type 18 | APT | + | 12357 |
| 10. Strep. pyogenes, A. Type 22 | APT | + | 10403 |
| 11. Aerobacter aerogenes | BHI | − | 884 |
| 12. Escherichia coli | BHI | − | 26 |
| 13. Salmonella enteritidis | BHI | − | 13076 |
| 14. Pseudomonas aeruginosa | BHI | − | 7700 |
| 15. Klebsiella pneumoniae | BHI | − | 9590 |
| 16. Salmonella typhimurium | BHI | − | 13311 |
| 17. Haemophilus influenzae | BHI | − | 9333 |
| 18. Strep. mitis | APT | + | 6249 |
| 19. Proteus vulgaris | BHI | − | 13315 |
| 20. Shigella dysenteriae | BHI | − | 11835 |
| 21. Diplococcus pneumoniae | APT | + | 6303 |
| 22. Propionibacter acnes Actinomyces (anaerobe) | Broth | + | 11827 |
| 23. Strep. sanguis | APT | + | 10556 |
| 24. Strep. salivarius | APT | + | 13419 |
| 25. Strep. mutans | BHI | + | 25175 |
| 26. Strep. agalactiae | APT | + | 13813 |

Cows were given daily injections of 5 ml samples of the polyvalent liquid vaccine. Antibody (IgG) titer levels for the injected cattle were determined periodically by taking optical density readings at 410 nm of antibody-containing fluid samples obtained from cow's milk.

EXAMPLE 1B

Preparation of Controlled Release Mixed Bacterial Vaccine.

Heat-killed bacteria were prepared in the manner described above. The polyvalent antigen obtained was microencapsulated by a conventional phase-separation process to prepare a polyvalent antigen-containing microparticle product. Generally, the antigen-containing shaped matrix materials are formed from polymers of biocompatible material, preferably biodegradable or bioerodable materials, preferably polylactic acid, polyglycolic acid, copolymers of lactic and glycolic acids, polycaptolactone, copolyoxalates, proteins such as collagen, fatty acid esters of glycerol, and cellulose esters. These polymers are well known in the art and are described, for example, in U.S. Pat. No. 3,773,919; U.S. Pat. No. 3,887,699; U.S. Pat. No. 4,118,470; U.S. Pat. No. 4,076,798; all incorporated by reference herein. The polymeric matrix material employed was a biodegradable lactide-glycolide copolymer.

Heat-killed bacterial antigens are encapsulated in such matrix materials, preferably as microspheres of between 1–500 microns diameter, preferably 10–250 microns. The encapsulation processes are conventional and comprise phase separation methods, interfacial reactions, and physical methods. Many combinations of matrices and many concentrations of assorted antigens may be employed, in order to provide for optimal rates of release of bacterial antigens to the host body from the microparticles. These combinations can be determined by those skilled in the art without undue experimentation.

The microparticles in the example were less than 250 microns in diameter. Approximately 750 mg of microparticles containing 22% (16.5 mg) of polyvalent antigen was then suspended in about 3 cc of a vehicle (1 wt. % Tween 20 and 2 wt. % carboxymethyl cellulose in water).

A small group of cattle was selected from a larger herd of cattle. Five of these randomly selected cattle were selected as controls. Four cattle were treated by an injection of microparticle-containing solution prepared as described above.

The four cows were injected intramuscularly with the polyvalent antigen-containing microparticles suspended in saline. The dose of antigen was over $2 \times 10^8$ bacterial cells per ml. Antibody (IgG) titer levels were determined periodically from samples of cows' milk obtained from the inoculated cows, as well as from the control cows.

EXAMPLE 1C

Preparation of Vaccine of Unknown Antigen Composition

We have discovered that bee honey contains a diverse group of antigens, the composition of which is unknown. The antigen in honey when injected in cows produces a hyperimmune state that results in maximum hypertensive properties of milk.

For example, a dose of 1 ml of honey diluted 1:5 in water was injected into 5 cows, once a week for 5 consecutive weeks, then once every 2 weeks for 6 months. Milk was collected between the third and sixth months for testing.

This example is included to illustrate the points that the exact composition of the antigen need not be known to practice the invention, and that any antigen or combination of antigens either known or unknown might be used to immune the cows for the production of the antihypertensive factor.

Testing of Hyperimmune Milk for Antihypertensive Activity

EXAMPLE 2

This was a double blind controlled study in which one experimental group of seven human volunteer subjects was fed hyperimmune milk product and a second control group of seven subjects was fed milk produced from nonhyperimmunized cows. Systolic blood pressures were measured both before and during treatment.

The study was divided into two phases, with a total duration of 14 weeks. The first phase was a 4-week pretreatment phase, at the end of weeks 1 and 4 of which systolic blood pressures were determined. The second phase consisted of a 10-week treatment period during which subjects consumed daily 50 g of powdered skim milk suspended in water, with blood pressure measurements being made at the end of weeks 2, 4, 6, 8 and 10. Those skilled in the art will know of pharmaceutically acceptable vehicles in which to suspend forms of milk protein.

The results of this study are shown both in Table 2 and FIG. 1, with Table 2 providing the raw data and FIG. 1 providing a comparison of the mean percent change in systolic blood pressure between the experimental and control groups. Systolic blood pressures of subjects ingesting the hyperimmune milk product decreased with time over the 10-week treatment period, with the decrease ranging between 5.3% to 8.40%. In contrast, with the control group fed non-hyperimmune milk product the changes were much smaller, ranging between 1% and 3.92% over the 10-week treatment period, but these changes were also related to length of treatment.

TABLE 2

| PATIENT # | −3 | 0 | 2 | 4 | 6 | 8 | 10 |
|---|---|---|---|---|---|---|---|
| IMMUNE MILK GROUP | | | | | | | |
| 1 | 135 | 128 | 128 | 124 | 118 | 110 | 116 |
| 2 | 128 | 126 | 120 | 118 | 118 | 116 | 108 |
| 4 | 120 | 125 | 118 | 115 | 110 | 106 | 112 |
| 18 | 150 | 124 | 124 | 127 | 127 | 130 | 120 |
| 19 | 128 | 138 | 126 | 130 | 128 | 128 | 122 |
| 21 | 116 | 110 | 115 | 100 | 100 | 112 | 116 |
| 7 | 118 | 105 | 98 | 98 | 108 | 102 | 108 |
| MEAN −> | | 127.86 | 122.29 | 116.00 | 117.00 | 114.86 | 114.57 |
| % change | 0.00 | 0.00 | 5.31 | 7.25 | 6.45 | 8.17 | 8.40 |
| NORMAL MILK GROUP | | | | | | | |
| 3 | 135 | 130 | 125 | 120 | 128 | 118 | 114 |
| 10 | 118 | 118 | 117 | 120 | 116 | 115 | 118 |
| 11 | 105 | 118 | 116 | 102 | 114 | 100 | 108 |
| 13 | 108 | 110 | 100 | 102 | 110 | 113 | 99 |
| 16 | 116 | 110 | 118 | 114 | 108 | 105 | 118 |
| 17 | 130 | 130 | 130 | 138 | 132 | 136 | 130 |
| 20 | 115 | 116 | 115 | 112 | 108 | 106 | 110 |
| MEAN −> | 118.14 | 118.86 | 117.29 | 115.43 | 116.57 | 113.29 | 113.86 |
| % change | 0.00 | 0.00 | 1.02 | 2.59 | 1.63 | 4.40 | 3.92 |

EXAMPLE 3

Figure 2:
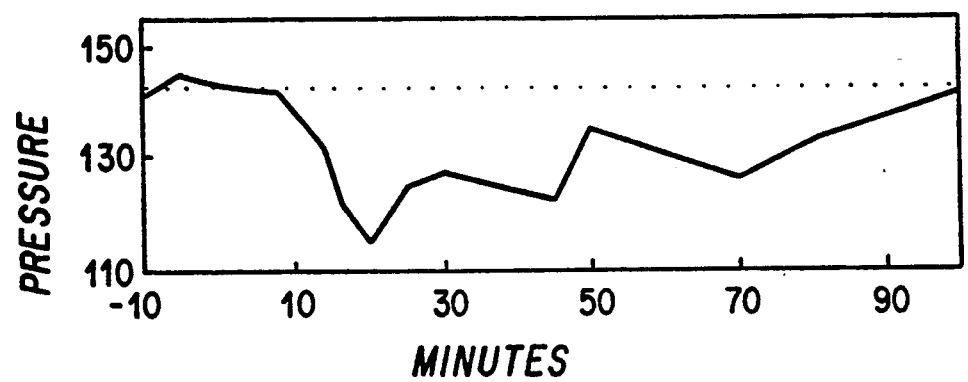
FIG. 2 shows the effect on human systolic blood pressure with time following intrabuccal absorption of a 5 mg dose of substantially pure milk anti-hypertensive factor.

In this experiment, 5 mg of partially purified MAF test material (see Example 4 for details of the isolation and purification of MAF) were placed directly on the tip of the tongue of a human volunteer subject, the systolic blood pressure determinations were made at 10 to 15-minute intervals over the next hour. The results of one such experiment are shown in FIG. 2. The systolic blood pressure-lowering effect was immediate and significant, causing a 30–40% drop in pressure within 30 minutes. This experiment was repeated several times with milk MAF obtained from cows treated with different antigens (see FIGS. 1A–1C). The results in each case were similar.

This procedure may be used for rapid screening of various milk fractions for MAF activity.

Isolation and Purification of Milk Antihypertensive Factor

EXAMPLE 4

STEP 1: Milk Filtrate Preparation

Twenty liters of fresh milk from normal or hyperimmunized cows were run through a cream separator (Delaval Model 102) to remove the fat.

The resulting 16 liters of skimmed milk were ultrafiltered to remove the high molecular weight species (>10,000 daltson) using a hollow fiber diafiltration/concentrator (Amicon DL-10L). The concentrator was equipped with two 10,000 dalton molecular weight cut-off cartridges. The skimmed milk was run at the pump speed of 80 on the meter and inlet and outlet pressure of 30 psi and 25 psi respectively.

Twelve liters of the filtrate (<10,000 daltons) coming out of the cartridges at the flow rate of four liters per hour was frozen or lyophilized for storage and for further purification.

STEP 2: Ion-Exchange Chromatography

The milk anti-hypertensive factor, MAF, in the filtrate was first isolated by an anion exchange chromatography column.

In this procedure, DEAE-Sepharose CL-6B gel (Pharmacial) was used to pack a 5×10 cm glass column which was equilibrated with sterile double distilled water, pH 7.0.

One liter of filtrate (<10,000 dalton fraction) was applied to the column and eluted with sterile double distilled water, pH 7.0, at the flow rate of 160 ml per hour. Ten millimeter fractions were collected and monitored at 280 nm in an LKB Uvicord 4700 absorptiometer with an optical density printed out on a connected recorded (Pharmacia REC-482).

The substances other than MAF having positive and neutral charges are not bound to the DEAE-Sepharose gel. They were eluted at the fall-through peak (first peak). The MAF carrying a negative charge was retained by the gel.

Figure 3:
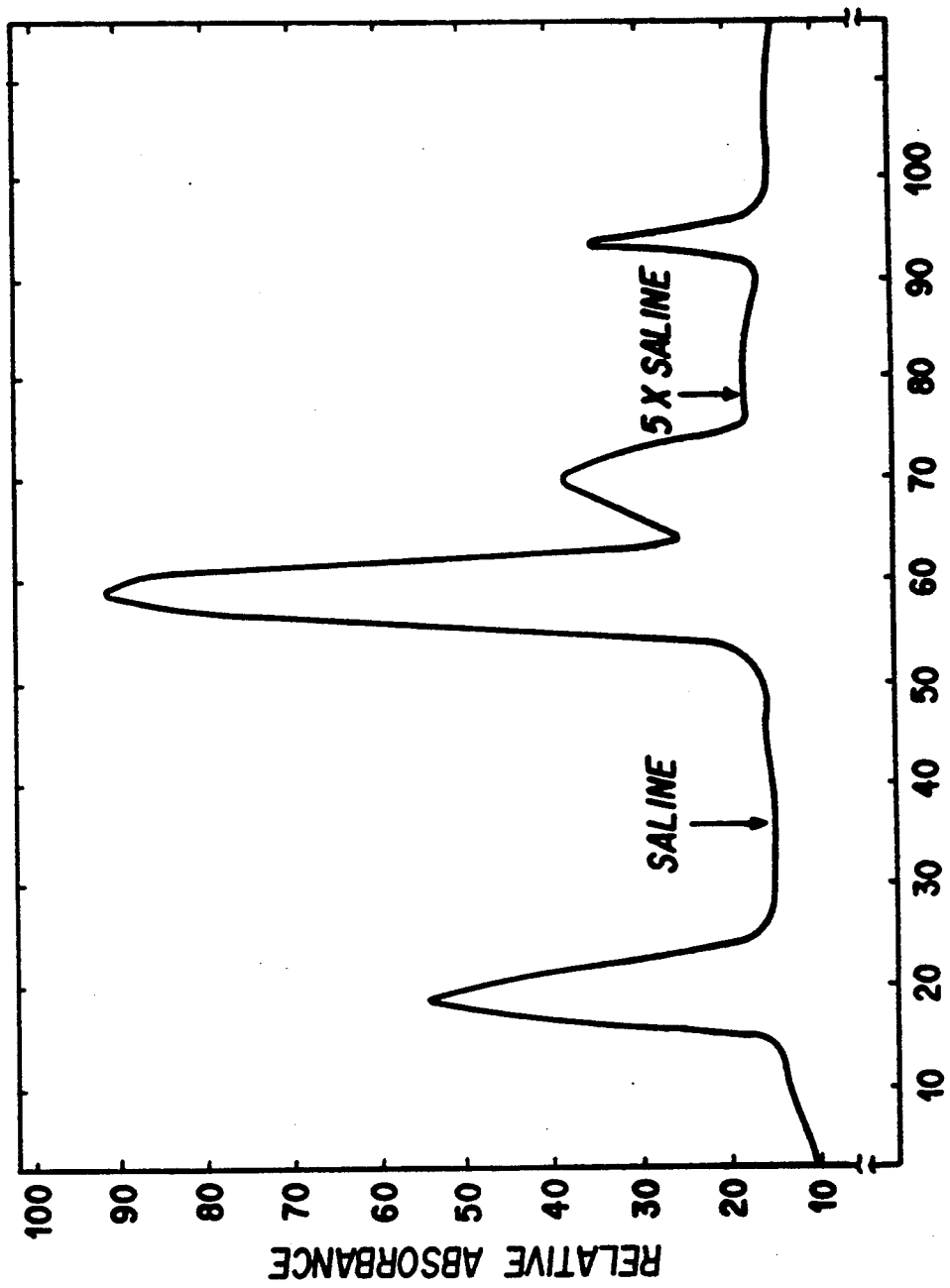
FIG. 3 shows the profile of elution with a salt gradient of milk antihypertensive factor from a DEAE-Sepharose CL-6B ion-exchange column (Step 2).

To elute the MAF, the column was eluted with a stepwise gradient using a sterile NaCl solution, pH 7.0. A typical profile is shown in FIG. 3. The second peak and its shoulder contained the MAF and other negatively charged species. The 20 ml fractions containing the second peak and its shoulder were pooled and lyophilized for storage and for further purification. Recovery studies showed that seven grams of dried powder were obtained.

STEP 3: Gel Filtration Chromatography

The fraction obtained from Step 2 was composed of MAF and other negatively charged components; therefore, an additional refining step was needed. To achieve further purification, it was necessary to use a gel filtration column to separate those negatively-charged components on the basis of molecular size and shape.

In this process, Sephadex G-10 resin (Pharmacia) was packed into a 2.5×80 cm glass column and equilibrated with sterile double distilled water, pH 7.0. Two grams of the MAF fraction from Step 2 were redissolved in sterile double distilled water and applied to the top of the column. The column was eluted at a flow rate of 30 ml per hour. Fractions of 3.3 ml were collected and monitored at 254 nm and 280 nm (Pharmacia Duo Optical Unit) with optical density printed out on a connected recorder (Pharmacia REC-482).

Figure 4:
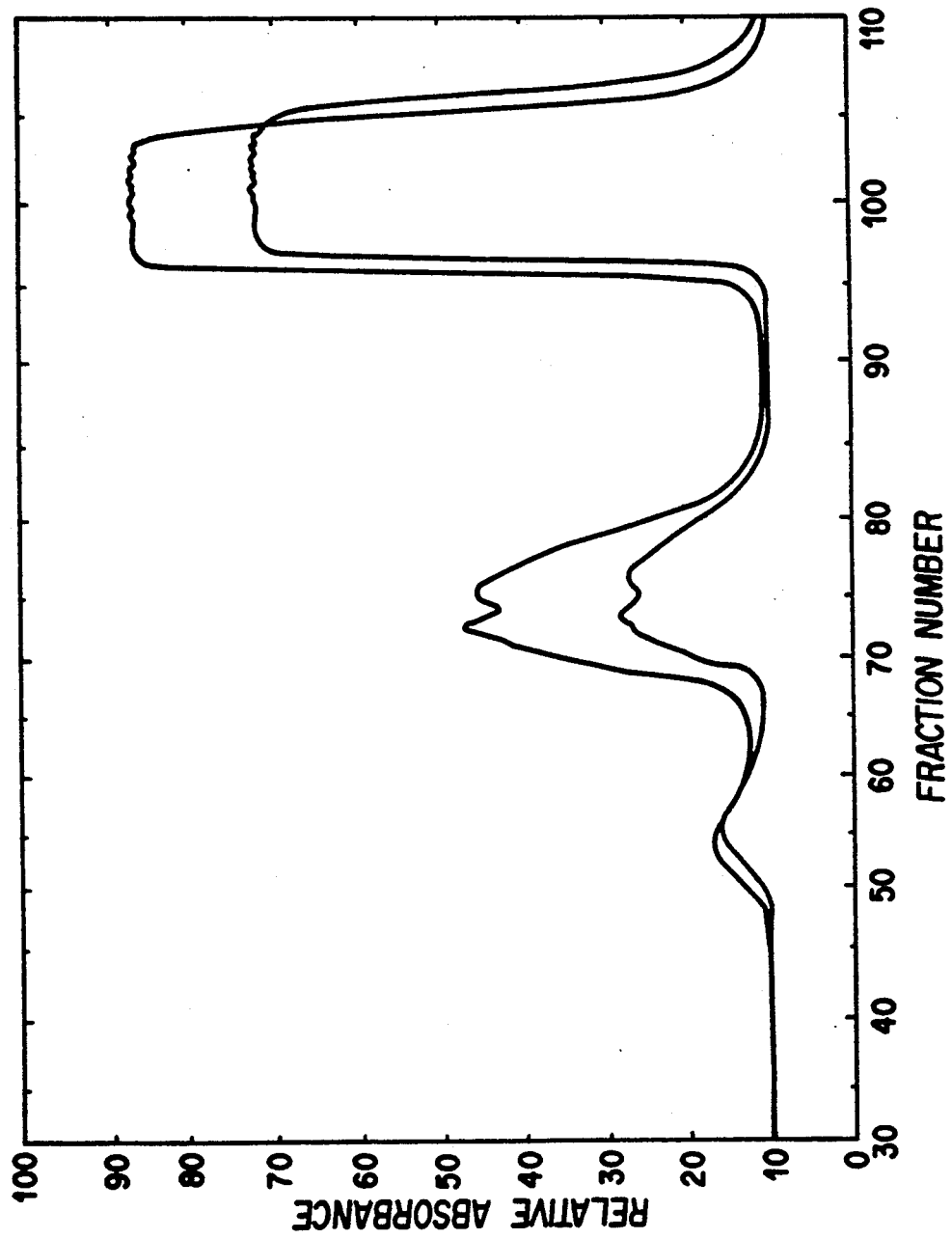
FIG. 4 shows the profiles of elutions with water of milk antihypertensive factor from a Sephadex G-10 molecular sieve column (Step 3).

There were 3 peaks in the elution profile, as shown in FIG. 4. The last peak, which is freed of large negatively charged substances, contained the MAF. Recovery studies showed a yield of 260 mg of dry powder from the overall process.

Having now generally described the invention, it will become readily apparent to those skilled in the art that many changes and modifications can be made thereto without affecting the spirit or scope thereof.

What is new and claimed and intended to be covered by Letters Patent of the United States is:

1. A composition for reducing elevated arterial blood pressure in an animal, wherein said composition is capable of reducing blood pressure in an animal, and wherein said composition comprises an anti-hypertensive factor from hyperimmune milk, wherein said anti-hypertensive factor has a molecular weight of less than 10,000 daltons and is negatively charged at pH 7.0, wherein said anti-hypertensive factor elutes in the third eluting peak of a Sephadex G10 column as shown in FIG. 4 of Applicants' specification, wherein said anti-hypertensive factor does not aggregate in distilled water, and wherein said composition is free of anti-inflammatory factor eluting in the first and second eluting peaks of a Sephadex G10 column as shown in FIG. 4 of Applicants' specification.

2. The composition of claim 1, wherein said hyperimmune milk is produced in hyperimmune diary cows of the genus Bos.

* * * * *